(12) United States Patent
Hamprecht et al.

(10) Patent No.: US 6,169,184 B1
(45) Date of Patent: Jan. 2, 2001

(54) PROCESS FOR THE PRODUCTION OF SUBSTITUTED PHENYLPYRIDINES

(75) Inventors: Gerhard Hamprecht, Weinheim; Joachim Gebhardt, Wachenheim; Heinz Isak, Böhl-Iggelheim; Michael Rack, Heidelberg; Joachim Rheinheimer, Ludwigshafen; Peter Schäfer, Ottersheim, all of (DE)

(73) Assignee: BASF Aktiengesellschaft, Ludwigschafen (DE)

( * ) Notice: Under 35 U.S.C. 154(b), the term of this patent shall be extended for 0 days.

(21) Appl. No.: 09/254,456

(22) PCT Filed: Aug. 29, 1997

(86) PCT No.: PCT/EP97/04706

§ 371 Date: Mar. 10, 1999

§ 102(e) Date: Mar. 10, 1999

(87) PCT Pub. No.: WO98/11069

PCT Pub. Date: Mar. 19, 1998

(30) Foreign Application Priority Data

Sep. 12, 1996 (DE) .............................. 196 36 995

(51) Int. Cl.$^7$ .............................. C02D 24/72; C02D 24/84
(52) U.S. Cl. ............................................................ 546/345
(58) Field of Search ................................................ 546/345

(56) References Cited

FOREIGN PATENT DOCUMENTS

| 19636995 | 9/1996 | (DE) . |
| 56115776 | 9/1981 | (JP) . |
| 61-280474 | 6/1985 | (JP) . |
| 95/02580 | 1/1995 | (WO) . |

OTHER PUBLICATIONS

Sakamoto et al., *Tetrahedron Letters*, 33(37), 5373–74, 1992.
Zhu et al., *J. Org. Chem.*, 1991, 56, 1445–1453.
Winkler et al., *Synthesis*, 1995, 1419–1421.
Houben Weyl, Methoden der Org. Chemie, IV. Auflage, vol. 13/3a, pp. 636–653.
Furukawa et al. *Heterocycles*, 24(12), 1986, 3337–3340.
Wakabayashi et al., *Bull. Chem. Soc. Jpn.*, 62, 2338–2341, 1989.
Kawai et al., *Tetrahedron Letters*, 25(24), 2549–2552, 1984.
Reiffenrath et al., *Agnew. Chem. Int. Ed. Eng.*, 33(13), 1994, 1386–1389.
Baker et al., *Tetrahedron: Asymmetry*, 5(1), 45–48, 1994.
OAE, *Phosphorus and Sulfur*, 1987, vol. 34, pp. 123–132.
Casreact 112:158015, Wakabyashi, Bull Chem Soc Jph, 1989, vol. 62(7), pp. 2338–2341, abstract.*
Casreact 111:77825, abstract of Oae, Heterocycles, 1989, vol. 28(1), pp. 99–102.*
Casreact 109:230735, abstract of Oae, Phosphorus Sulfur, 1987, 34(3–4), pp. 123–132.*
Casreact 107:77587, abstract of Furukawa, Heterocycles, 1986, vol. 24(12), pp. 3337–3340.*

* cited by examiner

*Primary Examiner*—D. Margaret Seaman
(74) *Attorney, Agent, or Firm*—Keil & Weinkauf

(57) ABSTRACT

A process for preparing substituted phenylpyridines of the formula I comprises reacting substituted pyridines of the formula II with an aryl compound of the formula III.

24 Claims, No Drawings

PROCESS FOR THE PRODUCTION OF SUBSTITUTED PHENYLPYRIDINES

DESCRIPTION

The present invention relates to a novel process for preparing substituted phenylpyridines of the formula I

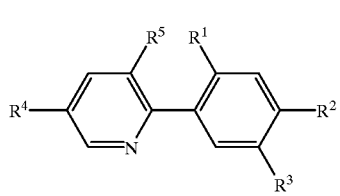

where
- $R^1$ is hydrogen, fluorine, chlorine or haloalkyl,
- $R^2$ is fluorine, chlorine or haloalkyl,
- $R^3$ is hydrogen, halogen or an organic radical that is inert under the reaction conditions,
- $R^4$ is alkyl, haloalkyl, halogen, alkylsulfonyl, haloalkylsulfonyl or haloalkoxy, and
- $R^5$ is hydrogen, halogen, haloalkyl, haloalkoxy, alkylsulfonyl or haloalkylsulfonyl.

The compounds I are intermediates for herbicides, but they can also be used as herbicides in their own right (WO-A 95/02580).

Various synthetic routes are known for preparing phenyl-substituted heterocycles. For instance, 2-bromopyridine can be converted using activated zinc into the corresponding 2-pyridylzinc bromide which can then be coupled with excess iodobenzene in a palladium-catalyzed reaction to give 2-phenylpyridine in moderate yield [THL 33 (1992) 5373; J. Org. Chem. 56 (1991) 1445].

This reaction requires bromoheterocycles which are often difficult to obtain; for example, according to JP-A 81/115776, 2-bromo-3-chloro-5-trifluoromethylpyridine, is obtained in a yield of only 10%. In addition, expensive iodine building blocks are required as aromatic component. Finally, owing to the high cost of the palladium catalyst, laborious recovery procedures are required.

Another method is coupling of a phenylboronic acid with an aromatic or heterocyclic bromine compound (Synthesis 1995, 1421; WO 95/2580). Disadvantages of this method are the low-yield preparation of aromatic boronic acids (Houben Weyl, Methoden der Org. Chemie, IVth edition, Vol. 13/3a, p. 636), which have to be prepared from organometallic precursors, and the use of expensive palladium catalysts.

In addition to halogens, sulfoxides and sulfones are known as further heterocycle leaving groups. According to JP-A 61/280,474, 2-sulfonylpyridines can be coupled with arylmagnesium compounds, but an additional halogen substitution in the Grignard moiety is not mentioned. According to Heterocycles 24 (1986), p. 3337, an additional halogen substitution in the pyridyl sulfone reduces the yield of coupling product, whereas a donor substitution of the Grignard reagent increases the yield.

Pyridyl sulfoxides as leaving groups in the uncatalyzed coupling with Grignard reagents usually only afford bipyridyls [Bull. Chem. Soc. Jpn. 62 (1989) 2338; THL 25 (1384) 2549]. Only in the case of 2-quinoline sulfoxide could the coupling product be isolated at all, in a 20% yield.

It is an object of the present invention to provide a generally applicable process for preparing substituted phenylpyridines of the formula I in high yields and purity from easily obtainable starting materials.

We have found that this object is achieved by a process for preparing substituted phenylpyridines of the formula I, which substituted pyridines of the formula II comprises reacting with an aryl compound of the formula III, if appropriate in the presence of a transition metal catalyst.

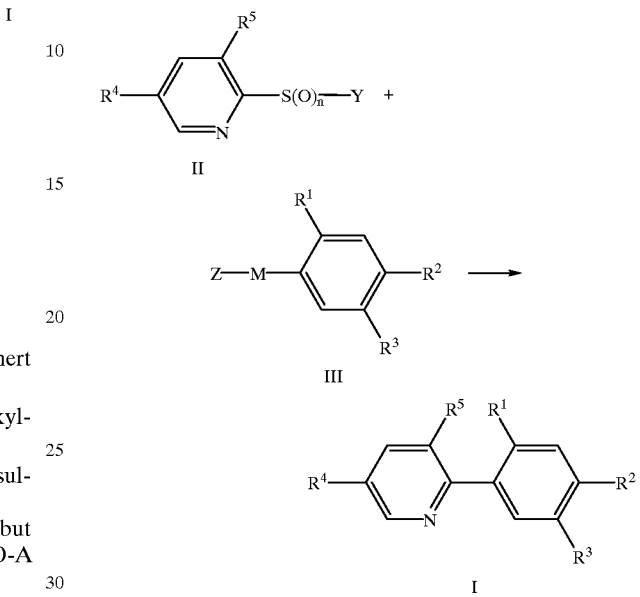

The substituents of the formulae II and III are as defined for the formula I; additionally:
- n is 1 or 2, and
- Y is alkyl, alkenyl or alkynyl, each of which may be substituted by halogen or methoxy; or is cycloalkyl or phenylalkyl; or substituted or unsubstituted phenyl or naphthyl,
- M is magnesium or zinc, and
- Z is halogen.

Starting materials for the process according to the invention are pyridine derivatives of the formula II which can be obtained for example from 2-halopyridines by reaction with suitable thiolates and subsequent oxidation. With or without transition metal catalysis, they are reacted with Grignard reagents or zinc compounds of the formula III to give phenylpyridines of the formula I.

If $R^1$ in the formula III is fluorine, the compounds III can for example be obtained by formation of a Grignard reagent from the correspondingly substituted o-fluorobromobenzene with magnesium at from −10 to 60° C.

The molar ratios in which the starting materials II and III are reacted with each other can, for example, be within the range from 0.9 to 1.5, preferably from 1.0 to 1.2, for the ratio of phenyl derivative III to pyridine compound II. The concentration of the starting materials in the solvent is not critical; it is for example from 0.1 to 5 mol/l, preferably from 0.5 to 2 mol/l.

Suitable solvents for these reactions are hydrocarbons, such as pentane, hexane, heptane, cyclohexane, toluene or chlorobenzene, and preferably solvents having electron donor character, in particular solvents having one or more ether oxygens, such as diethyl ether, diisopropyl ether, dibutyl ether, methyl tertbutyl ether, dimethoxyethane, diethoxyheptane, ethylene glycol dimethyl ether, furan, 5,6-dihydro-4H-pyran, tetrahydrofuran, tetrahydropyran, 1,3- dioxane, 1,4-dioxane, 4-methyl-1,3-dioxane, anisole, formaldehyde dimethyl acetal, formaldehyde diethyl acetal, acetaldehyde dimethyl acetal, acetaldehyde diethyl acetal, and furthermore triethylamine, hexamethylphosphoric triamide, 1,2-bis(dimethylamino)ethane, N-ethylmorpholine, tribenzylphosphine oxide, dimethyl sulfidre, dimethyl sulfoxide, dimethyl sulfone, tetramethylene sulfone, N-methylpyrrolidone or dimethylacetamide. Often, it is advantageous to use mixtures for example of ethers with amines or amides. It may also be advantageous to mix the polar component, for example from 1 to 3 mol % of tetrahydrofuran, triethylamine or N-ethylmorpholine, as an additive into the less polar component, for example benzene, toluene, xylene or naphthalene.

The conversion can be accelerated by the addition of a catalyst, for example of a transition metal. Suitable transition metal catalysts are iron compounds, cobalt compounds, nickel compounds, rhodium compounds, palladium compounds or platinum compounds, in particular nickel(0) compounds, nickel(II) compounds, palladium(0) compounds and palladium(II) compounds. Thus, salts such as nickel chloride, palladium chloride, palladium acetate or even complexes may be used. The only precondition is that the palladium ligands can be displaced by the substrate under the reaction conditions. Phosphine ligands, for example arylalkyl phosphines, such as inter alia methyldiphenylphosphine or isopropyldiphenylphosphine, triarylphosphines, such as inter alia triphenylphosphine, tritolylphosphine or trixylylphosphine, and trihetarylphosphines, such as trifurylphosphine, or dimeric phosphines are particularly suitable. Olefinic ligands, such as inter alia dibenzylideneacetone or salts thereof, cycloocta-1,5-diene or amines such as trialkylamines (for example triethylamine, tetramethylethylenediamine, or N-methylmorpholine) or pyridine are likewise well suited.

If a complex is used this can be employed directly in the reaction. This method can be used for example with bis(triphenylphosphine)nickel(II) bromide, bis(triphenylphosphine)nickel(II) chloride, [1,3-bis(diphenylphosphine)propane]nickel(II) chloride, [1,2-bis(diphenylphosphine)ethane]nickel II) chloride, tetrakistriphenylphosphinepalladium(0), bistriphenylphosphinepalladium dichloride, bistriphenylphosphinepalladium diacetate, a dibenzylideneacetonepalladium(0) complex, tetrakismethyldiphenylphosphinepalladium(0) or bis(1,2-diphenylphosphinoethane)palladium dichloride. Alternatively, a suitable ligand can be added to a nickel or palladium salt, thus forming the catalytically active complex in situ. This method is advantageous for example for the abovementioned salts and phosphine liganils, such as trifurylphosphine or tritolylphosphine. Furthermore, nickel complexes or palladium complexes, such as tris(dibenzylideneacetone)dipalladium, bis(dibenzylideneacetone)palladium or 1,5-cyclooctadienepalladium dichloride can be further activated by adding ligands such as trifurylphosphine or tritolylphosphine.

Customarily, from 0.001 to 12 mol %, in particular from 001 to mol %, of catalyst are used, based on the starting materials. It is possible to use larger amounts, but this is normally not necessary.

The reaction can be carried out under atmospheric or superatmospheric pressure, either continuously or batchwise.

Work-up after the reaction is carried out in a manner known per se; for example the reaction mixture is extracted with water to remove the salts, and the organic phase is dried and purified, for example by chromatography or distillation. However, it is also possible to concentrate the organic phase directly and to digest the residue in a solvent.

The process according to the invention affords the coupling product in high yields, even if both substrates carry more than one halogen substituent—something the literature has always considered disadvantageous, When substituted pyridyl sulfoxides of the formula II (n=1) are employed, the main products of the process according to the invention are the phenylpyridines I and not, as was to be expected from the literature [Bull. Chem. Soc. Jpn. 62 (1989) 2338], bipyridyl coupling products.

Essential for the process according to the invention is the presence of a sulfinyl or sulfonyl radical on the pyridine component. This leaving group ensures a particularly smooth conversion with exceptionally high selectivity if $R^1$ to $R^5$ are further reactive substituents.

A preferred embodiment of the process according to the invention is the reaction of a pyridine derivative of the formula II where Y is alkyl or aryl with a Grignard reagent of the formula IIIa.

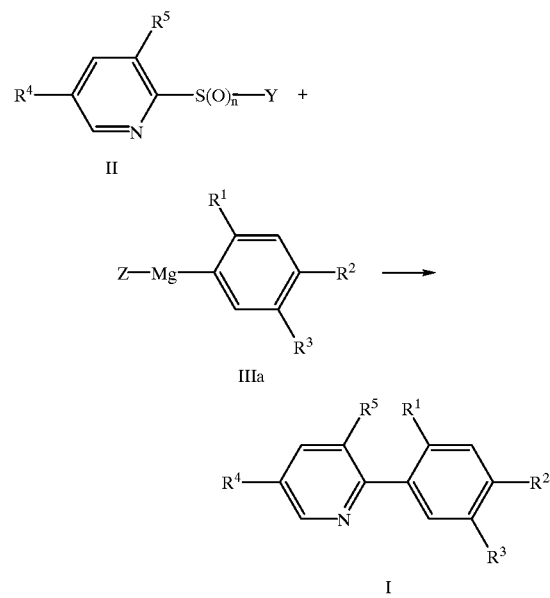

Advantageously, the pyridine compound II is, if appropriate together with a catalyst, initially charged in a solvent and the Grignard component IIIa is then added. However, the Grignard reagent can also be initially charged in one of the above-mentioned solvents—advantageously the solvent used in the Grignard synthesis—and the pyridine derivative II can then be added, if appropriate together with a catalyst. In a particular embodiment of the process according to the invention, the pyridine derivative II is added toward the end of the addition, for example under HPLC control, until it is only just consumed. Thus, the reaction is carried out under the conditions of a titration and the isolation of the end products from the starting materials is facilitated. Advantageously, the addition is carried out at a temperature of from −20 to 50° C., in particular from 10 to 30° C. The reaction time depends, inter alia, on he choice of the solvent and the substituents and is normally from 0.1 to 16 hours, in particular from 0.5 to 6 hours at from 10 to 140° C., in particular from 20 to 80° C.

A particularly preferred embodiment of the process according to the invention is the coupling of, for example, the 2-alkyl- or 2-arylsulfonyl-3-chloro-5- trifluoromethylpyridine of the formula II' or the corresponding 2-aryl sulfoxides of the formula II' with 2-chloro-4-fluoroanisole-5-magnesium bromide IIIa' to give 2-(4-chloro-2-fluoro-5-methoxyphenyl)-3-chloro-5-trifluoromethylpyridine.

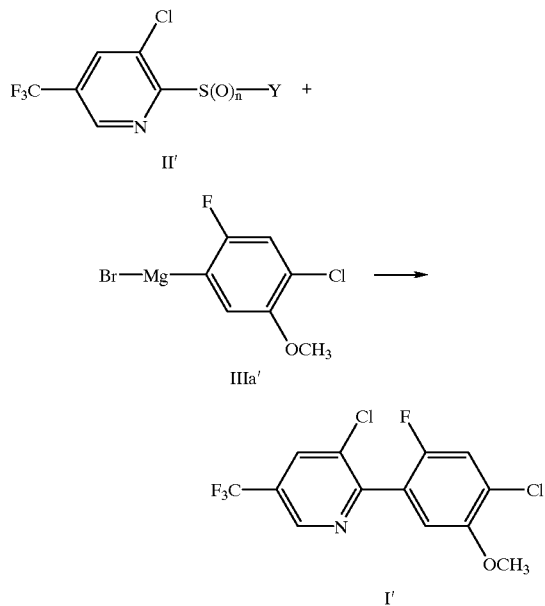

Advantageously, the reaction is carried out in the presence of a solvent at from −20 to 140° C., preferably from 20 to 80° C., and in an advantageous embodiment of the process according to the invention using the pyridine derivatives of the formulae IIa, IIb or IIc.

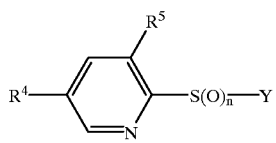

IIa: Y = aryl, n = 2
IIb: Y = alkyl, n = 1
IIc: Y = aryl, n = 1 very high yields of end products I are obtained even without employing catalysts.

In a further embodiment of the process according to the invention, the alkyl- or arylsulfonyl- or -sulfinylpyridines of the formula II are reacted with an arylzinc halogen compound of the formula IIIb.

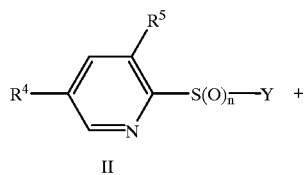

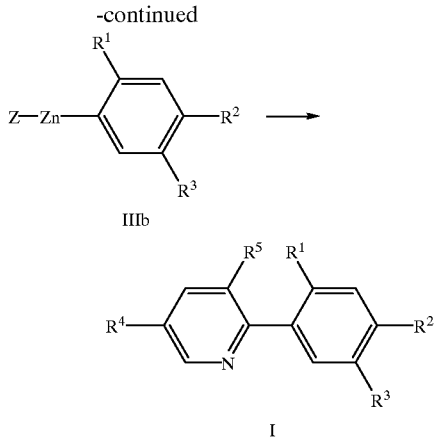

The reactions are carried out as described above, and in an advantageous embodiment of the process according to the invention using the pyridine derivatives of the formulae IIa, IIb or IIc, very high yields of end products I are obtained even without employing catalysts.

The compounds IIIb are prepared from the aryl-Grignard compounds IIIa described above, which are reacted in a manner known per se with zinc bromide or zinc chloride. This reaction can be carried out advantageously as a "one-pot synthesis" directly after the formation of the Grignard compound, the temperature being from −40 to 50° C., in particular from 15 to 30° C. This mixture can then be employed directly for the coupling, which may or may not be transition metal catalyzed, so that the entire sequence can be carried out in one reaction vessel.

For cost reasons, the easily obtainable unsubstituted derivatives will be preferred. The substituents on Y are not critical for the process according to the invention.

In the definitions of the compounds set forth at the beginning general terms are used which represent the following radicals:

Aliphatic radicals are, for example, alkyl, cycloalkyl, alkenyl or alkynyl.

Alkyl is generally $C_1$–$C_{10}$-alkyl, preferably $C_1$–$C_6$-alkyl and in particular $C_1$–$C_4$-alkyl. This also applies to alkyl combinations, such as alkoxy or haloalkyl. The radicals may carry further substituents inert under the reaction conditions.

Cycloalkyl is $C_3$- to $C_6$-cycloalkyl.

Alkenyl is $C_2$–$C_6$-alkenyl and alkynyl is $C_2$–$C_6$-alkynyl. This also applies to combinations such as alkenyloxy or alkynyloxy. The radicals may carry further substituents inert under the reaction conditions.

Aryl is generally phenyl or naphthyl or substituted phenyl or substituted naphthyl, for example substituted with 1 to 3 halogens, $C_1$- to $C_4$-alkyl, such as methyl or halomethyl, such as trifluoromethyl and/or $C_1$- to $C_4$-alkoxy.

Phenylalkyl is benzyl, 1- or 2-phenylethyl.

With regard to the intended use of the phenylpyridines of the formula I, those compounds are preferred where $R^3$ has the following meanings:

Hydrogen, halogen, an aliphatic or cycloalphatic radical or aryl, where the organic radicals mentioned may be attached to the phenyl ring via $CH_2$, C(O), C(O)O, O, S, C(O)$NR^6$ or $NR^6$ bridges and where $R^6$ is hydrogen, alkyl, alkenyl, alkynyl or aryl and two alkyl radicals may be linked by a bond or an oxygen to form a 5- or 6-membered ring.

For $R^3$, particular preference is given to:
hydrogen, halogen, alkyl, alkenyl, alkynyl, alkoxy, alkenyloxy, alkynyloxy, alkylthio, alkenylthio or alkynylthio; cycloalkyl; CH=CR$^6$R$^7$; alkylsulfonyloxy; haloalkylsulfonyloxy; arylsulfonyloxy; dialkylaminosulfonyloxy; alkoxysulfonyl; dialkylaminosulfonyl; aryloxysulfonyl or arylalkylaminosulfonyl; alkoxycarbonyl; dialkylaminocarbonyl; CR$^8$(U-alkyl) (V-alkyl); U-P-(V)-WR$^9$XR$^{10}$; aryl, aryloxy or arylthio; alkylarylamino-, alkenylarylamino- or alkynylarylaminocarbonyloxy; dialkylamino-, alllylalkenylamino-, alkylalkynylamino-, dialkenylamino- or dialkynylaminocarbonyloxy, where, in the case of dialkylaminocarbonyloxy, the two alkyl radicals may be linked by a bond or an oxygen to form a 5- or 6-membered ring; alkyl-, alkenyl-, alkynylcarbonyloxy or alkoxy-; alkenyloxy- or alkynyloxycarbonylalkoxy, NR$^{10}$R$^{11}$ or NR$^{11}$OR$^{10}$, where R$^6$ is halogen or alkyl, R$^7$ is formyl, alkoxycarbonyl or P(V)WR$^9$XR$^{10}$, R$^8$ is hydrogen or alkyl, R$^9$ is alkyl, R$^{10}$ is alkyl, alkenyl, alkynyl or aryl, R$^{11}$ is alkyl, alkenyl, alkynyl, formyl, alkanoyl, alkylsulfonyl or arylsulfonyl, U, V are independently of each other oxygen and/or sulfur and W, X are independently of each other oxygen, sulfur and/or alkylamino.

The meanings given above for the substituents R$^1$ to R$^{11}$ in the formula I are collective terms for a detailed list of the individual group members. All hydrocarbon chains, i.e. all alkyl, alkenyl, alkynyl, haloalkyl and haloalkoxy moieties, may be straight-chain or branched.

Substituents for the phenylpyridines of the formula I are in particular those below:

halogen fluorine, chlorine, bromine and iodine, preferably fluorine and chlorine;

alkyl, for example C$_1$–C$_6$-alkyl, such as methyl, ethyl, n-propyl, 1-methylethyl, n-butyl, 1-methylpropyl, 2-methylpropyl and 1,1-dimethylethyl;

alkenyl, for example C$_2$–C$_6$-alkenyl, such as ethenyl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl and 2-methylprop-2-en-1-yl, n-penten-1-yl, n-penten-2-yl, n-penten-3-yl, n-penten-4-yl, 1-methylbul-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimezhylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1ethyl-2-methylprop-1-en-1-yl and 1-ethyl-2-methyl-prop-2-en-1-yl, preferably ethenyl and prop-2-en-1-yl;

alkynyl, for example C$_2$–C$_6$-alkynyl, such as ethynyl, prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-in-5-yl, 4-methylpent-1-yn-1-yl, 4-methylpent-2-yn-4-yl and 4-methylpent-2-yn-5-yl, preferably prop-2-yn-1-yl and 1-methylprop-2-yn-1-yl;

haloalkyl, for example C$_1$–C$_6$-haloalkyl, such as alkyl as mentioned above which is partially or fully substituted by fluorine, chlorine and/or bromine, i.e. for example chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl or 4-bromobutyl;

alkoxy, for example C$_1$–C$_6$-alkoxy, such as methoxy, ethoxy, n-propoxy, 1-methylethoxy, n-butoxy, 1-methylpropoxy, 2-methylpropoxy or 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1ethylbutoxy, 2-ethylbutoxy 1,1,2-trimethylpropoxy, 1,2,2-trimethylpropoxy, 1-ethyl-1-methylpropoxy or 1-ethyl-2-methylpropoxy, haloalkoxy, for example C$_1$–C$_6$-haloalkoxy, such as alkoxy as mentioned above, which is partially or fully substituted by fluorine, chlorine, bromine and/or iodine, i.e. for example difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3- difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy or 1-(bromomethyl)-2-bromoethoxy, 2,2,3,3,4,4,4-heptafluorobutoxy, nonafluorobutoxy, 2-chlorofluorobutoxy, 3-chlorobutoxy or 4-chlorobutoxy, alkylthio, for example $C_1$–$C_6$-alkylthio, such as methylthio, ethylthio, n-propylthio, 1-methylethylthio, n-butylthio, 1-methylpropylthio, 2-methylpropylthio or 1,1-dimethylethylthio, alkylsulfinyl, for example $C_1$–$C_6$-alkylsulfinyl, such as methylsulfinyl, ethylsulfinyl, n-propylsulfinyl, 1-methylethylsulfinyl, n-butylsulfinyl, 1-methylpropylsulfinyl, 2-methylpropylsulfinyl or 1,1-dimethylethylsulfinyl, alkylsulfonyl, for example $C_1$–$C_6$-alkylsulfonyl, such as methylsulfonyl, ethylsulfonyl, n-propylsulfonyl, 1-methylethylsulfonyl, n-butylsulfonyl, 1-methylpropylsulfonyl, 2-methylpropylsulfonyl or 1,1-dimethylethylsulfonyl;

alkenyloxy, for example $C_2$–$C_6$-alkenyloxy, such as eth-1-en-1-yloxy, prop-1-en-1-yloxy, prop-2-en-1-yloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy or 2-methylprop-2-en-1-yloxy;

alkynyloxy, for example $C_2$–$C_6$-alkyayloxy, such as prop-1-yn-1-yloxy, prop-2-yn-1-yloxy, n-but-1-yn-1-yloxy, n-but-1-yn-3-yloxy, n-but-1-yn-4-yloxy or n-but-2-yn-4-yloxy;

cycloalkyl, for example $C_3$–$C_6$-cycloalkyl, such as cyclopropyl, cyclobutyl, cyclopentyl or cyclohexyl;

alkylamino, for example $C_1$–$C_6$-alkylamino, such as methylamino, ethylamino, n-propylamino, 1-methylethylamino, n-butylamino, 1-methylpropylamino, 2-methylpropylamino and 1,1-dimethylethylamino, preferably methylamino and ethylamino;

dialkylamino, for example di($C_1$–$C_6$-alkyl)amino, such as N,N-dimethylamino, N,N-diethylamino, N,N-dipropylamino N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl-N-methylamino, N-ethyl-N-propylamino, N-ethyl-N-(1-methylethyl)amino, N-butyl-N-ethylamino, N-ethyl-N-(1-methylpropyl) amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl) amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino, preferably dimethylamino and diethylamino; cyclopropylamino, cyclobutylamino, cyclopentylamino, cyclohexylamino, cycloheptylamino, cyclooctylamino, 1,2-, 1,3- or 1,4-oxazino.

The Examples which follow illustrate the invention.

1) Preparation of 2-(4-chloro-2-fluoro-5-methoxyphenyl)-3-chloro-5-trifluoromethylpyridine One fifth of the solution of 5.3 g (22 mmol) of 1-bromo-4-chloro-2-fluoro-5-methoxybenzene in 11 ml of tetrahydrofuran (THF) was added to 0.6 g (24.2 mmol) of magnesium turnings. After the onset of the reaction, the temperature was kept at from 29 to 31° C. The remainder of the solution was added dropwise within 1 h and stirring was continued at 30° C. for a further 40 min. Excess magnesium was separated off from the solution and washed with THF. At 0° C., this solution was added within 10 min to a mixture of 5.8 g (0.02 mol) of 3-chloro-2-n-propylsulfonyl-5-trifluoromethylpyridine and 0.65 g (1 mmol) of bis(triphenylphosphine)nickel(II) chloride in 25 ml of THF. The mixture was then stirred at 25° C. for a further 14 h. 50 g of ice and 150 ml of a saturated ammonium chloride solution were added to the reaction mixture, the solution was extracted and the organic phase was washed with saturated ammonium chloride solution. After having been dried and concentrated, the organic phase was chromatographed on silica gel using methylene chloride to give 8.2 g of a colorless crystalline material which contained 3.73 g (54.9%) of the title compound according to GC and NMR.
$^1$H-NMR (CDCl$_3$), δ=8.06 (s, 1H), 8.6 (s, 1H, pyridine), 65.97 (d, 1H), 7.25 (d, 1H, phenyl)

2) Preparation of 2-(4-chloro-2-fluoro-5-methoxyphenyl)-3-chloro-5-trifluoromethylpyridine from IIa A solution of 5.3 g (22 mmol) of 4-chloro-2-fluoro-5-methoxyphenylmagnesium bromide in 11 ml of THF, freshly prepared by the method of Example 1, was added with stirring at 0° C. within 5 minutes to a mixture of 6.4 g (0.02 mol) of 3-chloro-2-phenylsulfonyl-5-trifluoromethylpyridine and 0.065 g (0.1 mmol) of bis(triphenylphosphine)nickel(II) chloride in 25 ml of THF. Stirring was then continued at 25° C. for 1 h, another 0.065 g (0.1 mmol) of catalyst was added, and the mixture was stirred at 25° C. for a further 14 h. After work-up by the method of Example 1, 7.9 g of a crystalline material containing 4.4 g (64.7%) of the title compound according to GC and NMR analysis were obtained.

3) Preparation of 2-(4-chloro-2-fluoro-5-methoxyphenyl)-3-chloro-5-trifluoromethylpyridine from IIb 2.64 g (0.01 mol) of a Grignard solution of 4-chloro-2-fluoromethoxyphenylmagnesium bromide in 30 ml of THF, freshly prepared by the method of Example 1, were added at −15° C. within 5 min to a mixture of 2.55 g (0.01 mol) of 3-chloro-2-n-propylsulfinyl-5-trifluoromethylpyridine in 10 ml of THF, causing the mixture to warm to −5° C. After warming the mixture to 25° C., stirring was continued for 2.5 h while monitoring the reaction using HPLC. The reaction mixture was then treated with 50 g of ice and 100 ml of saturated ammonium chloride solution and extracted with ether. The extract was washed with saturated ammonium chloride solution, dried and filtered through neutral aluminum oxide and completely eluted with methylene chloride. After concentration, 2.2 g of a viscous oil containing 1.9 g (56% of theory) of the title compound by NMR and GC analysis were obtained.

4) Preparation of 2-(4-chloro-2-fluoro-5-methoxyphenyl)-3chloro-5-trifluoromethylpyridine from IIa At 20° C., 5 ml of a solution of 13.8 g (57.5 mmol) of 1-bromochloro-2-fluoro-5-methoxybenzene in 25 ml of THF were added to 1.46 g (60.4 mmol) of magnesium under nitrogen. After the onset of the reaction, the remainder of the abovementioned solution was added at from 28 to 30° C. within 20 min. After rinsing with THF, the mixture was stirred at from 30 to 25° C., for 2 h, initially with cooling. The Grignard solution obtained in this way was added under nitrogen at from 20 to 25° C. within 15 min to a mixture of 15.1 g (47 mmol) of 3-chloro-2-phenylsulfonyl-5-trifluoromethylpyridine in 45 ml of THF. The progress of the reaction was monitored using HPLC, and after stirring for 2.5 h at from 23 to 24° C., the reaction mixture was concentrated under reduced pressure. The residue was taken up in methylene chloride and extracted with 1N hydrochloric acid, 1N aqueous sodium hydroxide solution and water. The organic phase was concentrated under reduced pressure and distilled at from 130 to 135° C./0.5 mbar. 14.9 g of a product of melting point 100 to 102° C. containing 13.7 g of the pure title compound by GC analysis were obtained.

Yield: 84.1% based on pyridine, 70.1% based on anisole

5) Preparation of 2-(4-chloro-2-fluoro-5-methoxyphenyl)-3-chloro-5-trifluoromethylpyridine from IIc At from 20 to 25° C., a solution of 13.9 g (43.9 mmol) of 3-chloro-2-phenylsulfinyl-5-trifluoromethylpyridine in 25 ml of THF was added within 15 min to a Grignard solution of 1.3 g (52.9 mmol) of magnesium and 12.1 g (50.4 mmol) of 1-bromo-4-chloro-2-fluoro-5-methoxybenzene prepared by the method of Example 1. After the mixture had been stirred for 2 hours at 24° C., the reaction solution was poured on ice water, acidified with 4N hydrochloric acid and extracted with methylene chloride. The organic phase was washed with 1N aqueous sodium hydroxide solution and water, dried and filtered through silica gel. 16.3 g of a mixture of melting point 87 to 90° C. containing 12.1 g of the title compound by GC analysis were obtained.

Yield: 81% based on pyridine, 70.4% based on anisole

We claim:

1. A process for the preparation of a phenylpyridine of formula I

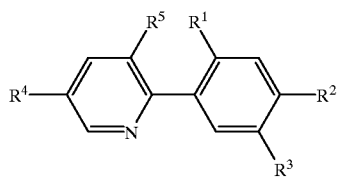

wherein $R^1$ is hydrogen, fluorine, chlorine or haloalkyl, $R^2$ is fluorine, chlorine or haloalkyl, $R^3$ is hydrogen, halogen or an organic radical that is inert under the reaction conditions, $R^4$ is alkyl, haloalkyl, halogen, alkylsulfonyl, haloalkylsulfonyl or haloalkoxy, and $R^5$ is halogen, haloalkyl, haloalkoxy, or haloalkylsulfonyl, which comprises reacting a pyridine of formula II

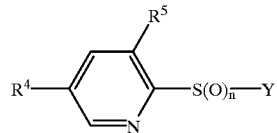

wherein n is 1 or 2, and

Y is alkyl, alkenyl or alkynyl, each of which is unsubstituted or substituted by halogen or methoxy; or is cycloalkyl or phenylalkyl; or unsubstituted or substituted phenyl or naphthyl, with an aryl compound of formula III

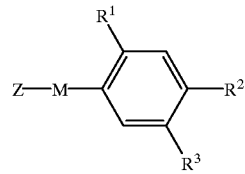

where

M is magnesium or zinc and

Z is halogen.

2. The process of claim 1, wherein the reaction is carried out in the presence of a transition metal catalyst.

3. The process of claim 1, wherein Y is alkyl which is unsubstituted or substituted by halogen or methoxy; or is unsubstituted or substituted phenyl.

4. The process of claim 1, wherein M denotes magnesium.

5. The process of claim 1, wherein M denotes zinc.

6. The process of claim 4, wherein the aryl compound of formula III is reacted with a pyridine of formula IIa, IIb or IIc

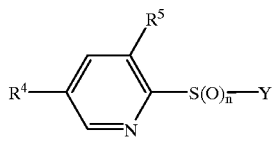

IIa: Y = aryl, n = 2
IIb: Y = alkyl, n = 1
IIc: Y = aryl, n = 1.

7. The process of claim 5, wherein the aryl compound of formula III is reacted a pyridine of formula IIa, IIb or IIc

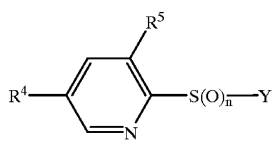

IIa: Y = aryl, n = 2
IIb: Y = alkyl, n = 1
IIc: Y = aryl, n = 1.

8. The process of claim 2, wherein the catalyst is a nickel(0) compound, a nickel(II) compound, a palladium(0) compound, or a palladium(II) compound.

9. The process of claim 2, wherein the catalyst is a palladium(0) compound or a palladium(II) compound or a mixture thereof.

10. The process of claim 2, wherein Y is alkyl which is unsubstituted or substituted by halogen or methoxy; or is unsubstituted or substituted phenyl.

11. The process of claim 2, wherein M denotes magnesium.

12. The process of claim 2, wherein M denotes zinc.

13. The process of claim 11, wherein the aryl compound of formula III is reacted with a pyridine of formula IIa, IIb or IIc

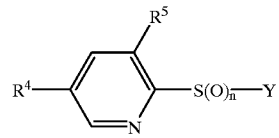

IIa: Y = aryl, n = 2
IIb: Y = alkyl, n = 1
IIc: Y = aryl, n = 1.

14. The process of claim 12, wherein the aryl compound of formula III is reacted with a pyridine of formula IIa, IIb or IIc

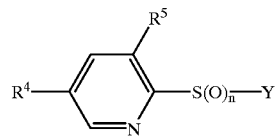

IIa: Y = aryl, n = 2
IIb: Y = alkyl, n = 1
IIc: Y = aryl, n = 1.

15. The process of claim 1, wherein at least one of $R^1$ to $R^5$ is a substituent capable of reacting with a Grignard reagent.

16. The process of claim 1, wherein $R^1$ is fluorine.
17. The process of claim 1, wherein $R^2$ is chlorine.
18. The process of claim 1, wherein $R^4$ is trifluoromethyl.
19. The process of claim 1, wherein $R^5$ is halogen.
20. The process of claim 2, wherein at least one of $R^1$ to $R^5$ is a substituent capable of reacting with a Grignard reagent.
21. The process of claim 2, wherein $R^1$ is fluorine.
22. The process of claim 2, wherein $R^2$ is chlorine.
23. The process of claim 2, wherein $R^4$ is trifluoromethyl.
24. The process of claim 2, wherein $R^5$ is halogen.

* * * * *

UNITED STATES PATENT AND TRADEMARK OFFICE
CERTIFICATE OF CORRECTION

PATENT NO.   : 6,169,184 B1
DATED        : January 2, 2001
INVENTOR(S)  : Hamprecht et al.

It is certified that error appears in the above-identified patent and that said Letters Patent is hereby corrected as shown below:

Column 12,
Line 53, after "reacted" insert -- with --.

Signed and Sealed this

Twenty-fourth Day of August, 2004

JON W. DUDAS
*Director of the United States Patent and Trademark Office*